United States Patent

Keefer et al.

[11] Patent Number: 5,212,204
[45] Date of Patent: May 18, 1993

[54] ANTIHYPERTENSIVE COMPOSITIONS AND USE THEREOF

[75] Inventors: Larry K. Keefer, Bethesda; David A. Wink, Frederick; Tambra M. Dunams, Frederick; Joseph A. Hrabie, Frederick, all of Md.

[73] Assignee: The United States of America as represented by the Department of Health and Human Services, Washington, D.C.

[21] Appl. No.: 423,279

[22] Filed: Oct. 18, 1989

[51] Int. Cl.$^5$ .......................................... A61K 31/135
[52] U.S. Cl. .................... 514/647; 514/649; 514/929
[58] Field of Search .............. 514/149, 499, 649, 647, 514/929; 546/6

[56] References Cited

U.S. PATENT DOCUMENTS

| | | | |
|---|---|---|---|
| 2,635,978 | 4/1953 | Massengale | 514/499 |
| 2,954,314 | 9/1960 | Metzger et al. | 514/499 |
| 3,309,373 | 3/1967 | Danzig | 546/6 |

OTHER PUBLICATIONS

Palmer et al. Nature 327, 524–526, 1987.
Kruszyna et al. Toxicology and Applied Pharmacology 91, 429–438, 1987.
Ignarro the FASEB Journal 3, 31–36, 1989.
Ignarro et al. J. of Pharmacology & Experimental Theraputics 218(3), 739–749, 1981.
Alston et al. J. Biol. Chem. 260(7), 4069–4074, 1985.
Kubrina et al. Izvestiia Akademii Nauk SSSR Seriia Biologicheskaia 6, 844–850, 1988.
Drago "Free Radicals in Inorganic Chemistry", No. 36, Advances in Chemistry Series, Amer. Chem. Soc., Wash. DC, 1962, pp. 143–149.
Wiersdorff et al. Chemical Abstracts 77:48034f, 1972.
Fujitsuka et al. Chemical Abstracts 82: 31108p, 1975.
World Patents Index Acc. No.: 80-59226c/34 JP 87017561 B (Apr. 18, 1987), abstracts of Jap. Patent.
"Pharmaceutics and Pharmacy Practice", eds Banker and Chalmers, J. B. Lippincott Co., Philadelphia, 1982, pp. 238–250.
ASHP "Handbook on Injectable Drugs" 4th ed., Trissel, pp. 622–630.
A. F. Vanin et al., Chem. Abstract 113:224354h (1990).
A. F. Vanin et al., Biokhimiya (Moscow) vol. 55, No. 2, pp. 1408–1413 (1990), with an English language Abstract.

*Primary Examiner*—Frederick E. Waddell
*Assistant Examiner*—K. Weddington
*Attorney, Agent, or Firm*—Birch, Stewart, Kolasch & Birch

[57] ABSTRACT

This invention concerns antihypertensive compositions and a method of lowering blood pressure in mammals. The active component of the compositions is a compound of the formula:

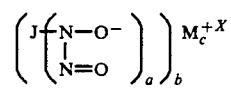

wherein J is an organic or inorganic moiety, $M^{+x}$ is a pharmaceutically acceptable cation and the compound decomposes under physiological conditions to release nitric oxide (NO).

27 Claims, No Drawings

ANTIHYPERTENSIVE COMPOSITIONS AND USE THEREOF

INTRODUCTION

This invention concerns novel pharmaceutical compositions and a method of treating hypertension. Related compositions and methods are described in U.S. Pat. Nos. 4,954,526 and 5,039,705.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24, 175-197, 1984.) Recently, Palmer et al., have shown that EDRF is identical to the simple molecule, nitric oxide, NO. (Nature 317, 524-526, 1987.) It has been hypothesized for years that many nitrovasodilators, which mimic the effect of EDRF, like glyceryl trinitrate, amyl nitrite, $NaNO_2$ and sodium nitroprusside (SNP), do so by virtue of their conversion to a common moiety, namely NO, which is also a vasodilator. (See Kruszyna et al., Tox. & Appl. Pharmacol.,91, 429-438, 1987; Ignarro, FASEB J. 3, 31-36, 1989, and Ignarro et al., J. Pharmacol. Exper. Theraputics 218(3), 739-749, 1981.) It has now been discovered that compounds containing the N-oxy-N-nitrosoamine group, $N_2O_2^-$ (also known as the N-nitrosohydroxylamine group) of the structure:

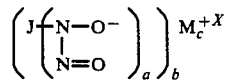
I and wherein the compound decomposes under physiological conditions to release NO, are potent anti-hypertensives. The compounds are useful for treating cardiovascular disorders in which lowering the blood pressure has a beneficial result. It is believed that these compounds function by releasing NO in the blood after injection. Alston et al. have shown that NO is generated by in vitro enzymatic oxidation of N-hydroxy-N-nitrosoamines (J. Biol. Chem. 260(7), 4069-4074, 1985) and Kubrina et al. have shown in vivo formation of nitrogen oxide upon injection with ammonium N-oxy-N-nitrosoaminobenzene (cupferron) into experimental animals( Izvestiia Akademii Nauk SSSR Seriia Biologicheskaia 6, 844-850, 1988).

While these compounds are, for the most part, known, there is no suggestion in the prior art that they are anti-hypertensive, indeed, there is no suggestion in the prior art that this general class of compounds has any pharmaceutical use (except for alanosine and dopastin, see below). They are described by Drago in "Free Radicals in Inorganic Chemistry" Advances in Chemistry Series, Number 36, American Chemical Society, Wash. DC, 1962, pages 143-149, which is incorporated by reference in its entirety. The reference is of a theoretical nature and mentions no utility whatsoever. Danzig et al., U.S. Pat. No. 3,309,373, discloses many of the compounds of formula I. Danzig teaches many possible utilities of his compounds, including their use as curing agents in rubber manufacture, antiknock additives for gasoline, indicator dyes, explosives, corrosion inhibitors and as fungicides for agriculture. Danzig et al. is incorporated by reference in its entirety. Wiersdorff et al (Chemical Abstracts 77:48034f, 1972) discloses that compounds of formula I, wherein J is a substituted phenyl, are useful as complexing agents and as fungicides. Fujitsuka et al. (Chemical Abstracts 82:31108p, 1975) discloses that compounds wherein J is phenyl, p-hydroxyphenyl and cyclohexyl are useful as polymerization inhibitors. Japanese patent JP 87017561 B, 4/18/87, discloses that the compounds wherein J is an aromatic hydrocarbon radical or sulfite ($-O_3S-$) are antibiotics for nitrifying bacteria and are added to industrial waters to control the bacteria. This patent does not teach the in vivo use of the compounds. Massengale, U.S. Pat. No. 2,635,978, discloses that compounds wherein J is optionally substituted phenyl are useful as fungicides for treating seeds, plants and fruits. Metzger et al., U.S. Pat. No. 2,954,314, discloses that compounds wherein J is an aliphatic, arylaliphatic or cycloaliphatic group are useful as fungicides for the external treatment of plants, leather, paper etc. Both Massengale and Metzger et al. are incorporated by reference in their entirety. None of the references cited above teach that compounds of formula I are antihypertensives, indeed none of these references teach any in vivo pharmaceutical utility of these compounds. There are two compounds that have in vivo pharmaceutical utility and contain the N-oxy-N-nitrosoamine moiety. These are alanosine, a potential anticancer drug with the structure

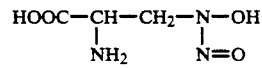

and dopastin, a dopamine beta-hydroxylase inhibitor of structure

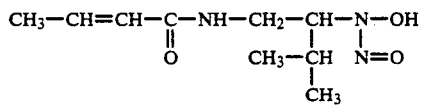

These compounds were not known to be antihypertensive previously. The applicant has disclosed the antihypertensive utility of the compounds wherein J is a primary or secondary amine in U.S. Pat. Nos. 4,954,526 and 5,039,705 respectively.

SUMMARY OF THE INVENTION

The present invention provides pharmaceutical compositions comprising: a compound of the following formula

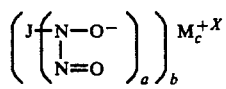
I wherein J is an organic or inorganic moiety, $M^{+x}$ is a pharmaceutically acceptable cation, wherein x is the valence of the cation, a is 1 or 2, b and c are the smallest integers that result in a neutral compound, and wherein the compound decomposes under physiological conditions to release nitric oxide (NO); and a pharmaceutically acceptable carrier; with the proviso that the compound of formula I not be a salt of alanosine or dopastin. Another object of the invention is a method of treating cardiovascular disorders by lowering the blood pressure by administering a compound of formula I.

DETAILED DESCRIPTION OF THE INVENTION

By J being an organic or inorganic moiety is meant that J is any moiety that results in a compound of formula I that will decompose under physiological conditions to release nitric oxide. This decomposition product is the active agent. By physiological conditions is meant the chemical, physical and biological conditions found in the body at the point of administration or after distribution of the compound by the blood system. Since injection into the bloodstream is the preferred method of administration, those compounds that decompose in the blood system to release NO are preferred. Some of the compounds, such as the diethylamine-nitric oxide adduct (U.S. Pat. No. 5,034,705) spontaneously decompose in water (however not too fast to limit its usefulness), others such as cupferron appear to be enzymatically decomposed (see Alston et al. supra). There are both physico-chemical and biological limitations on the compounds of formula I. Since the compounds are mostly used intraveneously, they should be at least somewhat soluble in aqueous solution, with the help of solubilizing agents or organic solvents. Thus compounds where J is a large hydrophobic moiety, such as a $C_{20}$ paraffin or an anthracyl moiety are excluded, since such a compound would not be soluble enough in aqueous solution to be useful. The other limitation on J is that the compound or its decomposition products should not be so acutely toxic at the doses administered that the subject is endangered.

Preferred J moieties are: A) a = 1, and J is $-O_3S-$(sulfite), $-O-$(oxide), $C_1-C_{12}$ aliphatic, $C_3-C_8$ cycloalkyl, benzyl, phenyl, substituted benzyl, substituted phenyl, benzylcarbonyl, phenylcarbonyl, substituted benzylcarbonyl, substituted phenylcarbonyl, $C_1-C_{12}$ acyl, and

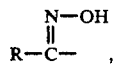

wherein R is $C_1-C_{12}$ aliphatic, $C_3-C_8$ cycloalkyl, benzyl, phenyl, substituted benzyl or substituted phenyl, and said substituted benzyl or substituted phenyl being substituted with one or two substituents selected from the group consisting of halogen, hydroxy, $C_1-C_4$ alkyl, $C_1-C_4$ alkoxy, amino, mono-$C_1-C_4$ alkylamino, di-$C_1-C_4$ alkylamino, phenyl and phenoxy; B) 1a=2 and J is para-phenylene;

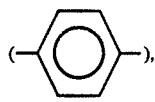

$C_2-C_{12}$ alkylene, $-CHR_1-$, wherein $R_1$ is H or $C_1-C_{12}$ aliphatic, and

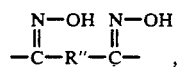

wherein R" is $C_1-C_6$ alkylene.

By aliphatic is meant a straight chain or branched chain, saturated or unsaturated, acyclic hydrocarbon moiety. By acyl is meant an aliphaticcarbonyl moiety. By alkyl and alkoxy is meant both straight and branched chain. By alkylene is meant a divalent straight or branched chain saturated acyclic hydrocarbon bridging group such as $-CH_2CH_2-$ or $-CH_2CH(CH_3)-$. By halogen is meant F, Cl, Br, and I, preferably F, Cl, and Br. For aliphatic and alkyl moieties the preferred number of carbon atoms is 1–4. For cycloalkyl the preferred ring size is 5 and 6. For acyl moieties the preferred number of carbon atoms is 2–6.

More preferred J moieties are: A) a=1, and J is $-O_3S-$, $-O-$, $C_1-C_{12}$ alkyl, $C_5-C_6$ cycloalkyl, benzyl, phenyl or

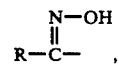

wherein R is $C_1-C_{12}$ alkyl, $C_5-C_6$ cycloalkyl, benzyl or phenyl; B) a=2, and J is para-phenylene, $C_2{14} C_4$ alkylene or $-CHR_1-$, wherein $R_1$ is H or $C_1-C_6$ alkyl.

The most preferred J moieties are $-O_3S-$, $-O-$ or phenyl when a=1, and para-phenylene when a=2.

By pharmaceutically acceptable cation is meant any cation that does not render the compound unstable or insoluble in water or toxic at the doses contemplated; these cations are well known to one of ordinary skill in the pharmaceutical arts. Generally the cation will be a group 1 or group 2 ion, such as sodium, potassium, calcium or magnesium ions, or $NR_2R_3R_4R_5^{30}$, wherein $R_2$, $R_3$, $R_4$ and $R_5$ are independently selected from the group consisting of H, $C_1-C_4$ alkyl, $C_5-C_6$ cycloalkyl, benzyl or phenyl. The most preferred cations are $Na^+$, $K^{30}$, $Ca^{+2}$, $Mg^{+2}$ and $NH_4^{30}$.

The subscripts b and c in formula I mean the number of the particular ion to be found in the empirical formula of the salt. The smallest whole number that results in an electrically neutral compound is used. Thus, if the anion is $ON_2O_2^{-2}$ and the cation is $Na^+$ then b is 1 and c is 2.

SYNTHESIS

The methods used to make the compounds of formula I are all known or easily derivable from known methods. Massengale, U.S. Pat. No. 2,635,978, teaches how to make the compounds where J is phenyl or substituted phenyl in examples 1–8. Danzig, U.S. Pat. No. 3,309,373, teaches how to make the compounds wherein J is paraphenylene in examples I–III, V, VII and IX. He teaches how to make the compounds where J is

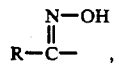

and R is phenyl or alkyl in examples XII, XIII, XV, XVII and XVIII. Danzig teaches how to make the compounds where J is a divalent alkylene moiety and a=2 in the paragraph bridging columns 16 and 17. Metzger et al., U.S. Pat. No. 2,954,314, discusses the compounds where J is aliphatic, arylaliphatic or cycloaliphatic. Drago(supra) discusses the Traube reaction which produces the compound containing the structure $(CH_2(N_2O_2)_2)^{-2}$. The Traube reaction can be generalized to produce the compounds containing the structure $$(R_1-CH(N_2O_2)_2)^{-2}$$

by starting with the alcohol of structure $R_1-CH_2CH_2OH$, wherein $R_1$ is defined above.

The compounds wherein J is an aliphatic, aryl or arylaliphatic moiety and $a=1$ are generally made by reducing the appropriate aliphatic, aryl or arylaliphatic nitro compound to the corresponding aliphatic, aryl or arylaliphatic hydroxylamine and nitrosating this compound to produce the corresponding aliphatic, aryl or arylaliphatic N-nitrosohydroxylamine ( also known as N-hydroxy-N-nitrosoamine)( see Massengale, supra and Alston et al., page 4070). This reaction sequence is shown below:

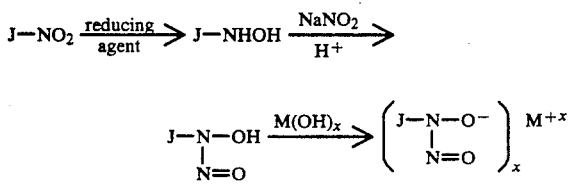

The same reaction scheme can be used to make the compounds wherein a is 2 and J is alkylene by starting with a dinitroalkyl compound, ie, $NO_2-CH_2CH_2-NO_2$ produces

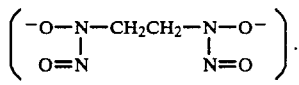

Cupferron, the compound of formula I wherein J is phenyl and $M^{+x}$ is $NH_4^+$, is commercially available from Aldrich Chemical Company, Milwaukee, Wi.

The compounds wherein $a=1$ and J is

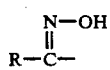

are made by starting with the corresponding aldoxime

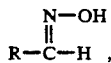

and reacting it with base $(M(OH)_x)$ and nitric oxide in a non-hydroxylic solvent as shown by the following reaction (see Danzig supra):

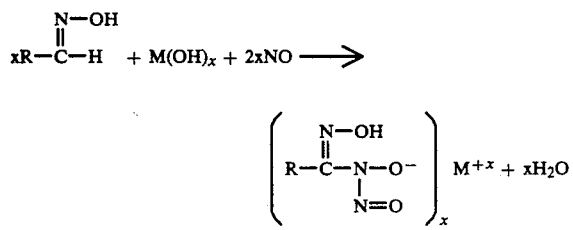

The following examples show the synthesis details for three of the compounds.

EXAMPLE 1

Angeli's salt, the disodium salt of hyponitric acid, $Na_2(ON_2O_2)$ was synthesized as follows. A concentrated solution of sodium ethoxide (18 g) in ethanol was added to a saturated solution of hydroxylamine hydrochloride (6 g) in ethanol. The sodium chloride precipitate was filtered off, and 8 g of ethyl nitrate was added to the filtrate at room temperature. A finely divided suspension of Angeli's salt was formed, the yield increasing as the liquid cooled. After several hours, the crystals were filtered and washed with ethanol. They were then recrystallized twice by dissolving them in 4 ml of water and adding a large excess of ethanol. The crystals (5 g) were finally dried by washing them with ether. The ether was removed under reduced pressure.

EXAMPLE 2

The potassium salt of the sulfite addition product of NO, $K_2(O_3SN_2O_2)$, was synthesized as follows. KOH (50 g) was dissolved in water (100 ml). The mixture was saturated with $SO_2$ at room temperature. The reaction mixture became warm. Additional KOH (60 g) was added. Nitric oxide was bubbled through the solution at room temperature. The mixture was stirred for 3 hours and the resultant crystals were suction filtered. The crystals were washed with water (20 ml), followed by washing with 95% ethanol and ether.

EXAMPLE 3

The disodium salt of p-phenylene-N-N'-dinitrosodihydroxylamine,

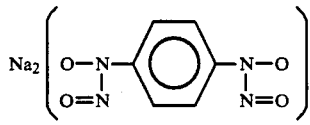

was prepared as follows. To a solution of sodium methoxide (3.9 g) in excess methanol was added 1,4-benzoquinone dioxime (5 g). The solution was cooled to $-78°$ C. and placed in a Parr low pressure hydrogenator modified by having a stainless steel tank, gauge, valves and tubing. The apparatus was subjected to three nitrogen flush/evacuation cycles to remove as much oxygen as possible. Nitric oxide, commercial grade, was bubbled through 10M NaOH and dried by passing it through a column containing NaOH pellets. This nitric oxide was admitted to the Parr apparatus continuously until absorption was complete (about 5 hr). The apparatus was shaken continuously during the addition of the nitric oxide. The nitric oxide was removed by flushing with nitrogen. The resultant product was isolated by filtration, washed and dried.

The cation, $M^{30\ x}$, can be changed by several well known methods. Most of the synthesis methods described above involve the use of a base as part of the reaction scheme, i.e., NaOH or NaOEt; the resultant salt contains the cation from the base used. By running the reaction with a different base, i.e., KOH, $NH_4OH$ or KOEt, a different cation is obtained. Alternatively, the cation in an already formed compound can be replaced by another cation by methods, such as a metathesis reaction, that are well known in the art; see, for example, Massengale, examples 3-8.

PHARMACOLOGICAL PROPERTIES

The effect on the mean arterial blood pressure and heart rate of male Sprague-Dawley rats of the compositions of the invention was measured using a standard technique. A pressure transducer (Bell and Howell, type 4-327-I) was connected to the right carotid artery via a catheter containing heparinized saline. The mean arterial pressure and heart rate were recorded on a Gould (Model 2800) 8-channel recorder. The rats were anesthetized with nembutal at an initial dose of 35 mg/kg body weight and recurrent smaller injections as needed. The compounds were dissolved in a pharmaceutical carrier and injected into the rats via a catheter in the right femoral vein. Table 1 shows the results.

TABLE 1

| Compound | Dose (μmole/kg) | Mean Arterial Pressure | | | Heart Rate | |
|---|---|---|---|---|---|---|
| | | Initial (mm Hg) | Post | Change | Initial (beats/min) | Post |
| A | 3.4 | 114 | 91 | −23 | 420 | 440 |
| A | 39.0 | 126 | 42 | −84 | 420 | 480 |
| B | 3.4 | 117 | 109 | −8 | 420 | 420 |
| B | 39.0 | 96 | 57 | −39 | 540 | 420 |
| C | 3.4 | 114 | 104 | −10 | 480 | 420 |
| C | 42.0 | 96 | 75 | −21 | 420 | 420 |
| D | 6.8 | 132 | 118 | −14 | 420 | 360 |
| D | 39.0 | 108 | 90 | −18 | 420 | 420 |
| SNP | 0.34 | 113 | 56 | −57 | 403 | 454 |
| NaNO$_2$ | 4.00 | 126 | 48 | −78 | 360 | 420 |
| NaNO$_3$ | 42.00 | 117 | 120 | 3 | 420 | 420 |

In Table 1, the pharmaceutical carrier was Abbott's 5% dextrose USP. Compound A is Angeli's salt, B is $K_2(O_3SN_2O_2)$, C is the disodium salt of p-phenylene-N,N'-dinitrosodihydroxylamine and D is cupferron. SNP(sodium nitroprusside), NaNO$_2$, and NaNO$_3$ were used as controls. SNP and NaNO$_2$ are known vasodilators. NaNO$_3$ is the oxidative breakdown product of NaNO$_2$ and has little vasodilatory effect. The results show that the compounds of formula I are potent antihypertensives, decreasing the blood pressure significantly. The peak value of the blood pressure decrease, shown in Table 1, takes only about 30 sec to 1 min to occur, after injection, and the blood pressure starts to rise again soon after and has totally recovered within 10-15 min.

The compositions of this invention are useful for treating any cardiovascular disorder that will respond favorably to a decrease in blood pressure. These disorders include chronic hypertension, hypertensive crisis (an acute hypertensive emergency), acute congestive heart failure, angina, acute myocardial infarction, left ventricular failure, cerebrovascular insufficiency and intracranial haemorrhage. Because of the fast response upon intravenous injection the compositions are particularly advantageous for treating acute disorders such as hypertensive crisis, toxemia of pregnancy and acute congestive heart failure. The preferred method of administration is by injection into the blood system, most preferably by intravenous injection. The chronic disorders can be treated by continuous intravenous infusion. A suitable dosage for intravenous administration is about 0.01 to 10.0 mg/kg per day.

The pharmaceutical compositions of the invention comprise the compounds of formula I and a pharmaceutical carrier. The carrier can be any of those conventionally used and is limited only by chemico-physical considerations such as solubility and lack of reactivity with the compound and by the route of administration. For intravenous administration, the carrier will be aqueous and may contain solubilizing agents, buffers, preservatives, antioxidants, chelating agents, and agents to control the tonicity, such as dextrose or sodium chloride. The requirements for effective pharmaceutical carriers for injectable compositions are well known to one of ordinary skill in this art. (See "Pharmaceutics and Pharmacy Practice", J. B. Lippincott Company, Philadelphia, 1982,edited by Banker and Chalmers, pages 238-250, which are incorporated by reference, also see ASHP "Handbook on Injectable Drugs" 4the edition by Trissel, pages 622-630, which lists commercially available intravenous infusion solutions, these pages are incorporated by reference.) The compounds may also be formulated as inclusion complexes, such as, for example, cyclodextrin inclusion complexes; or the compounds may be carried within liposomes. Preferred pharmaceutical carriers for injection are PBS (phosphate buffered saline), 5% dextrose and sterile water. Since the compounds of formula I are subject to being oxidized by oxygen, an antioxidant, such as ascorbate, can be added to the carrier to increase the shelf-life.

What is claimed is:

1. An injectable pharmaceutical composition consisting essentially of a compound of the formula

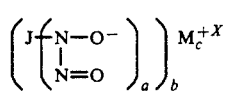

wherein J is an inorganic moiety, or an organic moiety selected from the group consisting of $C_1$-$C_{12}$ aliphatic, $C_3$-$C_8$ cycloalkyl, benzyl, phenyl, substituted benzyl, substituted phenyl, benzycarbonyl, phenylcarbonyl, substituted benzylcarbonyl, substituted phenylcarbonyl, $C_1$-$C_{12}$ acyl, and

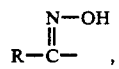

wherein R is $C_1$-$C_{12}$ aliphatic, $C_3$-$C_8$ cycloalkyl, benzyl, phenyl, substituted benzyl or substituted phenyl, and said substituted benzyl and substituted phenyl is substituted with one or two substituents selected from the group consisting of halogen, hydroxy, $C_1$-$C_4$ alkyl, $C_1$-$C_4$ alkoxy, amino, mono $C_1$-$C_4$ alkylamino, di $C_1$-$C_4$ alkyl-amino, phenyl and phenoxy;

$M^{+x}$ is a pharmaceutically acceptable cation, wherein x is the valence of the cation, a is 1, b and c are the smallest integers that result in a neutral compound, and wherein the compound decomposes under physiological conditions to release nitric oxide (NO); and a pharmaceutically acceptable sterile carrier.

2. An injectable pharmaceutical composition consisting essentially of a compound of the formula

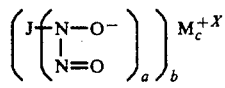

wherein J is an inorganic moiety or an organic moiety; $M^{+x}$ is a pharmaceutically acceptable cation, wherein x is the valence of the cation, a is 2, b and c are the smallest integers that result in a neutral compound, and wherein the compound decomposes under physiological conditions to release nitric oxide (NO); and a pharmaceutically acceptable sterile carrier.

3. The pharmaceutical composition of claim 2, wherein J is a para-phenylene, $C_2$–$C_{12}$ alkylene, —CHR$_1$—, wherein R$_1$ is H or $C_1$–$C_{12}$ aliphatic, or

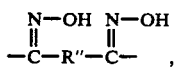

wherein R″ is $C_1$–$C_6$ alkylene.

4. The pharmaceutical composition of claim 1, wherein J is $^-O_3S$—, —O—, $C_1$–$C_{12}$ alkyl, $C_5$–$C_6$ cycloalkyl, benyzl, phenyl or

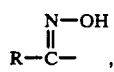

wherein R is $C_1$–$C_{12}$ alkyl, $C_5$–$C_6$ cycloalkyl, benzyl or phenyl.

5. The pharmaceutical composition of claim 4, wherein J is $^-O_3S$—, —O— or phenyl.

6. The pharmaceutical composition of claim 5, wherein $M^{+x}$ is a group I ion, a group II ion or $^+NR_2R_3R_4R_5$, wherein $R_2$, $R_3$, $R_4$ and $R_5$ are independently chosen from the group consisting of H, $C_1$–$C_4$ alkyl, $C_5$–$C_6$ cycloalkyl, phenyl and benzyl.

7. The pharmaceutical composition of claim 6, wherein $M^{+x}$ is Na$^+$, K$^+$, Ca$^{+2}$, Mg$^{+2}$ or NH$_4^+$.

8. The pharmaceutical composition of claim 3, wherein $M^{+x}$ is a group I ion, a group II ion or $^+NR_2R_3R_4R_5$, wherein $R_2$, $R_3$, $R_4$ and $R_5$ are independently selected from the group consisting of H, $C_1$–$C_4$ alkyl, $C_5$–$C_6$ cycloalkyl, phenyl and benzyl.

9. The pharmaceutical composition of claim 8, wherein $M^{+x}$ is Na$^+$, K$^+$, Ca$^{+2}$, Mg$^{+2}$ or NH$_4^+$.

10. The pharmaceutical composition of claim 1, wherein the compound of formula I is

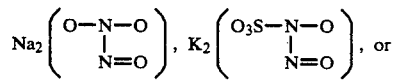

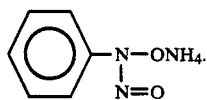

11. The pharmaceutical composition of claim 2, wherein the compound of formula I is

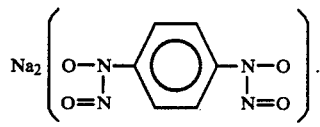

12. The pharmaceutical composition of claim 1, wherein the pharmaceutically acceptable carrier is pure sterile water, phosphate buffered saline or an aqueous glucose, solution.

13. The pharmaceutical composition of claim 2, wherein the pharmaceutically acceptable carrier is pure sterile water, phosphate buffered saline or an aqueous glucose solution.

14. The pharmaceutical composition of claim 3, wherein the pharmaceutically acceptable carrier is pure sterile water, phosphate buffered saline or an aqueous glucose solution.

15. The pharmaceutical composition of claim 4, wherein the pharmaceutically acceptable carrier is pure sterile water, phosphate buffered saline or an aqueous glucose solution.

16. A method of treating cardiovascular disorders in mammals by lowering the blood pressure comprising: administering to a mammal in need thereof a blood pressure lowering effective amount of a compound of the formula

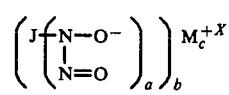

wherein J is an organic or inorganic moiety, $M^{+x}$ is a pharmaceutically acceptable cation, wherein x is the valence of the cation, a is 1 or 2, b and c are the smallest integers that result in a neutral compound, and wherein the compound decomposes under physiological conditions to release nitric oxide (NO).

17. The method of claim 16 wherein the cardiovascular disorder is chronic hypertension, crisis, acute congestive heart failure, angina, acute myocardial infarction, left ventricular failure, cerebrovascular insufficiency or intracranial haemorrhage.

18. The method of claim 17 wherein the cardiovascular disorder is hypertensive crisis, acute congestive heart failure or acute myocardial infarction.

19. The method of claim 16 wherein a is 1 and J is selected from the group consisting of $^-O_3S$—, —O—, $C_1$–$C_{12}$ aliphatic, $C_3$–$C_8$ cycloalkyl, benzyl, phenyl, substituted benzyl, substituted phenyl, benzylcarbonyl, phenylcarbonyl, substituted benzycarbonyl, substituted phenylcarbonyl, $C_1$–$C_{12}$ acyl and

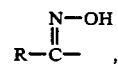

wherein R is $C_1$–$C_{12}$ aliphatic, $C_3$–$C_8$ cycloalkyl, benzyl, phenyl, substituted benzyl or substituted phenyl, said substituted benzyl and said substituted phenyl being substituted with one or two substituents selected from the group consisting of halogen, hydroxy, $C_1$–$C_4$ alkyl, $C_1$–$C_4$ alkoxy, amino, mono-$C_1$–$C_4$ alkylamino, di-$C_1$–$C_4$ alkylamino, phenyl and phenoxy.

20. The method of claim 16 wherein a is 2, and J is paraphenylene, $C_2$–$C_{12}$ alkylene, —CHR$_1$—, wherein R$_1$ is H or $C_1$–$C_{12}$ aliphatic, or

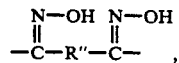

wherein R″ is $C_1$–$C_6$ alkylene.

21. The method of claim 19 wherein J is $^-O_3S$—, —O—, $C_1$–$C_{12}$ alkyl, $C_5$–$C_6$ cycloalkyl, benzyl, phenyl or

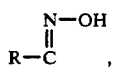

wherein R is $C_1$-$C_{12}$ alkyl, $C_5$-$C_6$ cycloalkyl, benzyl or phenyl.

22. The method of claim 21 wherein J is $-O_3S-$, $-O-$ or phenyl.

23. The method of claim 22 wherein $M^{+x}$ is a group I ion, a group II ion or $^+NR_2R_3R_4R_5$, wherein $R_2$, $R_3$, $R_4$, and $R_5$ are independently selected from the group consisting of H, $C_1$-$C_4$ alkyl, $C_5$-$C_6$ cycloalkyl, phenyl and benzyl.

24. The method of claim 23 wherein $M^{+x}$ is $Na^{30}$, $K^+$, $Ca^{+2}$, $Mg^{+2}$ or $NH_4^+$.

25. The method of claim 20 wherein $M^{+x}$ is a group I ion, a group II ion or $^+NR_2R_3R_4R_5$, wherein $R_2$, $R_3$, $R_4$ and $R_5$ are independently selected from the group consisting of H, $C_1$-$C_4$ alkyl, $C_5$-$C_6$ cycloalkyl, phenyl and benzyl.

26. The method of claim 25 wherein $M^{+x}$ is $Na^+$, $K^{30}$, $Ca^{+2}$, $Mg^{+2}$ or $NH_4^+$.

27. The method of claim 16 wherein the compound of formula I is

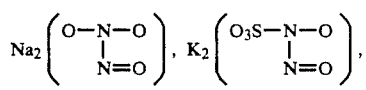

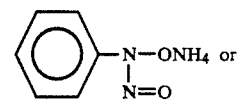

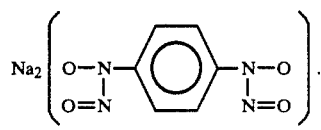

* * * * *